(12) United States Patent
Sarphie et al.

(10) Patent No.: US 6,558,961 B1
(45) Date of Patent: May 6, 2003

(54) IMMUNODIAGNOSTICS USING PARTICLE DELIVERY METHODS

(75) Inventors: David F. Sarphie, Oxfordshire (GB); Lee K. Roberts, Madison, WI (US); Deborah L. Fuller, Madison, WI (US)

(73) Assignee: PowderJect Research Limited, Oxford (GB)

( * ) Notice: Subject to any disclaimer, the term of this patent is extended or adjusted under 35 U.S.C. 154(b) by 0 days.

(21) Appl. No.: 09/389,390

(22) Filed: Sep. 3, 1999

Related U.S. Application Data

(60) Provisional application No. 60/099,261, filed on Sep. 4, 1998, and provisional application No. 60/139,045, filed on Jun. 10, 1999.

(51) Int. Cl.⁷ ............................................ G01N 33/533
(52) U.S. Cl. .................. 436/525; 436/501; 436/518; 436/506; 436/507; 436/513; 436/523; 436/529; 436/526; 436/532; 436/535; 436/811; 436/815; 424/130.1; 424/141.1; 424/142.1; 424/147.1; 424/154.1; 424/159.1; 424/160.1; 424/171.1; 424/275.1; 424/9.8; 424/9.81; 424/910; 600/306; 600/506; 600/12; 530/868
(58) Field of Search ................... 436/501, 506, 436/507, 513, 518, 523, 525, 529, 526, 532, 535, 811, 815; 424/130.1, 141.1, 142.1, 147.1, 154.1, 159.1, 160.1, 171.1, 275.1, 9.8, 9.81, 910; 600/306, 506, 12; 530/868

(56) References Cited

U.S. PATENT DOCUMENTS

| | | | | |
|---|---|---|---|---|
| 4,270,548 A | * | 6/1981 | Brennan | |
| 4,472,507 A | * | 9/1984 | Pluim, Jr. | 436/131 |
| 4,557,931 A | * | 12/1985 | Irie et al. | 424/88 |
| 5,032,401 A | * | 7/1991 | Jamas et al. | 424/426 |
| 5,043,158 A | * | 8/1991 | Sleytr et al. | 424/92 |
| 5,102,663 A | * | 4/1992 | Livingston et al. | 424/88 |
| 5,104,620 A | * | 4/1992 | Wiley et al. | |
| 5,283,321 A | * | 2/1994 | Bartfai | 530/403 |
| 5,470,708 A | * | 11/1995 | Yang et al. | 435/6 |
| 5,489,510 A | * | 2/1996 | Lopukhin et al. | 435/7.1 |
| 5,505,694 A | * | 4/1996 | Hubbard et al. | 604/51 |
| 5,531,925 A | * | 7/1996 | Landh et al. | 252/299.01 |
| 5,556,100 A | * | 9/1996 | Taylor et al. | 273/236 |
| 5,571,531 A | * | 11/1996 | McDermott et al. | 424/459 |
| 5,630,796 A | * | 5/1997 | Bellhouse et al. | 604/69 |
| 5,647,371 A | * | 7/1997 | White, Jr. et al. | |
| 5,692,518 A | * | 12/1997 | Baker et al. | 128/743 |
| 5,705,159 A | * | 1/1998 | Irie et al. | 424/185.1 |
| 5,735,288 A | * | 4/1998 | Fishman | 128/743 |
| 5,840,585 A | * | 11/1998 | Rodkey et al. | 436/161 |
| 5,869,103 A | * | 2/1999 | Yeh et al. | 424/501 |
| 5,939,046 A | * | 8/1999 | Halliday et al. | 424/9 |
| 6,010,478 A | | 1/2000 | Bellhouse et al. | 604/70 |
| 6,017,540 A | | 1/2000 | Srivastava et al. | 424/193.1 |
| 6,040,134 A | | 3/2000 | Madsen et al. | 435/4 |
| 6,053,889 A | | 4/2000 | Heinzen et al. | 604/68 |
| 6,080,539 A | * | 6/2000 | Zeytinoglu et al. | 435/5 |
| 6,087,163 A | * | 7/2000 | Gennaro et al. | 435/320.1 |

* cited by examiner

Primary Examiner—Christopher L. Chin
Assistant Examiner—Pensee T. Do
(74) Attorney, Agent, or Firm—Thomas P. McCracken

(57) ABSTRACT

Methods for assessing immunocompetence, cellular or humoral immunity, antigen exposure, or allergic conditions in an individual by accelerating diagnostic particles into a target skin site in the individual are provided.

31 Claims, No Drawings

IMMUNODIAGNOSTICS USING PARTICLE DELIVERY METHODS

CROSS-REFERENCE TO RELATED APPLICATIONS

This application is related to U.S. provisional patent application serial Nos. 60/099,261, filed Sep. 4, 1998, and 60/139,045, filed Jun. 10, 1999, from which applications priority is claimed pursuant to 35 U.S.C. §119(e)(1) and which applications are incorporated herein by reference in their entireties.

TECHNICAL FIELD

The present invention relates generally to particle-based immunodiagnostic methods. More particularly, the invention pertains to methods for assessing immunocompetence, antibody and cell mediated immunity, antigen exposure, or allergic conditions in an individual by accelerating diagnostic particles into a target skin site in the individual.

BACKGROUND OF THE INVENTION

Allergies represent one of the most common and well characterized immune disorders in humans, affecting roughly 20 percent of all individuals in the United States. Allergic reactions are generally immune reactions that are initiated by IgE-dependent stimulation of tissue mast cells and related effector molecules (e.g., basophils). Binding events between cell surface bound IgE molecules and antigen results in rapid release of biological response modifiers which bring about increased vascular permeability, vasodilation, smooth muscle contraction and local inflammation. This sequence of events is termed immediate hypersensitivity and begins rapidly, usually within minutes of exposure in a sensitized individual to antigen. In its most severe systemic form, anaphylaxis, such immediate hypersensitivity can bring about asphyxiation, produce cardiovascular collapse, and even result in death. Individuals that are prone to strong immediate hypersensitivity responses are referred to as "atopic" and are said to suffer from "allergies." Clinical manifestations of atopy include hay fever (rhinitis), asthma, urticaria (hives), skin irritation (e.g., chronic eczema), and related conditions.

A number of clinical test procedures for assessing allergies have been described and are known in the art. See generally American College of Physicians, "Allergy Testing," *Ann. Intern. Med.* (1989) 110:317–320; Bousquet, J. (1988) "*In Vivo Methods for Study of Allergy: Skin Tests, Techniques, and Interpretation,*" Allergy, Principals and Practice, $3^{rd}$ ed., Middleton et al., eds., CV Mosby Co., St. Louis, Mo., pp. 419–436; and Van Arsdel et al. (1989) *Ann. Intern. Med.* 110:304–312. These so-called "skin tests" or "scratch tests" involve introduction of antigens into the epidermis via skin prick or scratch, or introduction into the dermis via intracutaneous (intradermal) injection. An immediate wheal and flare reaction at the site of introduction (the classic atopic reaction) indicates antibody-mediated (IgE) hypersensitivity to the test antigen. More particularly, when a sensitized individual is challenged by an appropriate antigen in a skin or scratch test, the site of introduction becomes red from local vasodilation. In a second phase of the reaction, soft swelling occurs (the wheal) and, in a third phase, blood vessels at the margins of the wheal dilate and become engorged with red blood cells, producing a characteristic erythemic rim (the flare). The full wheal and flare reaction usually appears within 10 to 15 minutes of antigen administration, and generally subsides within about an hour. A wheal of sufficient size with accompanying flare represents a positive test for allergy against the antigen.

A related methodology can be used to assess cell mediated immune (CMI) responses in individuals immunized against, infected with or exposed to intracellular pathogens such as bacteria, viruses, or other microbes. In like manner, these techniques can be used to diagnose and/or identify the presence of neoplastic disease in individuals. More particularly, the delivery of recall antigens to diagnose preexisting immunity against, exposure to, or infection by various pathogens is known in the art. Recall antigens are immunogenic moieties (from a pathogen) which are capable of eliciting an antigen-specific CMI response in individuals that have been exposed to, are harboring, or have been immunized against the relevant pathogen. Most commonly, the antigen-specific CMI response is a delayed type hypersensitivity (DTH) response, a form of cell-mediated immunity in which the ultimate effector cell is the activated mononuclear phagocyte (macrophage).

In a commonly employed test, a relatively small amount of soluble purified protein derivative (PPD), a protein prepared from the *Mycobacterium tuberculosis* pathogen, is delivered to an individual via intradermal injection, and will elicit a DTH response in individuals recovering from primary tuberculosis or who have been vaccinated against tuberculosis. In this test, the classic DTH response evolves over a period of about 24 to 48 hours. Infiltration of T cells and blood monocytes at the injection site causes escape of fibrinogen from blood vessels to surrounding tissue where it is converted to fibrin. Fibrin deposition and accumulation of T cells and monocytes about the injection site causes local tissue swelling and hardening ("induration"), the hallmark of DTH. Induration is generally detectable by about 18 hours after antigen injection, and is maximal at 24 to 48 hours. The presence of sufficient induration and/or erythema at the injection site represents a positive test for exposure to or vaccination against the *Mycobacterium tuberculosis* pathogen.

Similar such testing procedures can be used to assess CMI responses to other microbial antigens, where detection of a suitable DTH response to a delivered antigen is used as an alternative to, or in conjunction with standard immunological methods of testing for serum antibody titers or serum antigen levels. These methods can also be used to assess neoplastic conditions, where the recall antigen is from a known tumor-associated antigen, and a positive test is indicative of the presence of neoplasia in the individual.

Such delayed type hypersensitivity testing can also be used to evaluate individuals suspected of having primary or acquired immune deficiency disorders in which cell-mediated immunity is decreased or absent. Turk, J. L. (1980) *Delayed Hypersensitivity,* in "Research Monographs in Immunology," Vol. 1, Elsevier/North Holland Biomedical Press, New York, N.Y. pp. 111–157. In this regard, loss of DTH responses to universally encountered antigens (e.g., candidal antigens) is indicative of T cell function deficiency, a clinical condition commonly termed "anergy." Anergic individuals are extremely susceptible to infection by microorganisms normally resisted by cellular immunity. Anergy, as shown by reduced or loss of DTH to one or more common antigens, has been used to assess malnutrition (Law et al. (1973) *Ann. Intern. Med.* 79:545–550), and depressed DTH responses can be used to assets conditions such as diabetes mellitus, uremia, and certain acquired immune deficiency disorders (Spitler et al. (1976) *Manual of Clinical Immunology,* Rose et al. Eds, A.S.M., Washington, D.C., pp53–63). Positive correlation between defective cell-mediated immunity and disseminated cancer, again as indicated by anergy to multiple skin test antigens, has also been reported. Johnson et al. (1979) *Amer. J. Surgery* 137:536–541; Lamb et al. (1962) *J. Immunol.* 89:555–558; Eilber et al. (1970) *Cancer* 25:362–367; Hersh et al. (1971) *N. Engl. J. Med.* 285:1211–1216; and Fass et al. (1970) *N. Engl. J. Med.* 282:776–780.

SUMMARY OF THE INVENTION

It is a primary object of the invention to provide methods for reliably and reproducibly assessing allergies, conditions of humoral and cellular immunity, conditions of anergy, and neoplasia in individuals using particle delivery methods to deliver antigens or allergens to target skin sites in an individual.

In one aspect of the invention, a method is provided for assessing a localized skin immune reaction against a selected agent in an individual. The method entails preparing particles which comprise an immunogenic moiety (e.g., an antigen) from the selected agent. The particles are accelerated into a target skin site in the individual, and the visual appearance of the target site is then assessed to determine the presence or absence of a skin reaction at or about the site of administration, wherein presence of the skin reaction is indicative of a humoral or cellular immune response against the selected agent.

In one embodiment, the method is used to assess a cell mediated immune (CMI) response against the selected agent. The particles are accelerated into the target skin site, and the target site is then assessed for a characteristic skin reaction involving induration and/or erythema, wherein presence of induration and/or erythema is indicative of a cell mediated immune response against the selected agent. In related embodiments, the method is used to assess a CMI response against an intracellular pathogen, such as a viral, parasitic or bacterial pathogen; or against agents that cause contact dermatitis. In other related embodiments, the method is used to diagnose or detect a neoplastic condition which expresses a known tumor-associated antigen. The particles are delivered into the epidermis or dermis of the individual using particle delivery techniques.

In another embodiment, the method is used to assess a humoral immune (antibody-mediated or complex-mediated) response against the selected agent. The particles are accelerated into the target skin site, and the visual appearance of the target site is then assessed for a localized skin immune reaction, typically involving localized inflammation, induration and/or erythema. The presence of such skin reaction at or around the site of particle administration is indicative of a humoral response against the selected agent. This method can be used to diagnose or assess certain allergic conditions (e.g., penicillin allergies); exposure to an infectious disease (e.g., malaria, hepatitis or meningitis); or autoimmune disorders (e.g., Rheumatoid arthritis, Systemic lupus erythematosus, multiple sclerosis, or Goodpasture's syndrome).

In another aspect of the invention, a method is provided for assessing an allergic (atopic) condition in an individual. The method entails preparing particles which comprise an allergen and accelerating the particles into a target skin site in the individual. The target site is then assessed to determine the presence or absence of a localized skin immune reaction, particularly an immediate hypersensitivity reaction which is characterized by the presence or absence of a wheal and flare at or around the site of particle administration. The presence of a wheal and flare of sufficient size is indicative of an allergic condition against the allergen.

In one embodiment, the method is used to assess an allergic (atopic) condition against a single allergen in the individual. In a related embodiment, the method is used to assess responsiveness against multiple allergens in the individual, wherein the method is repeated or otherwise performed to deliver several allergens to the individual in a single clinical visit and/or procedure. The allergens are generally delivered to a test area on the individual's back or volar aspect of the forearm and, if multiple allergens are delivered, the allergens can be delivered in rows or another pattern which facilitates reading of the test site for allergies or reactions to particular allergens.

In yet a further aspect of the invention, a method is provided for assessing the immunocompetence of an individual, or for clinically staging, diagnosing and/or monitoring a disease, disorder or condition in an individual. These methods rely on assessing a delayed type hypersensitivity (DTH) reaction or another localized skin immune reaction (e.g., formation of immune complexes) in the individual, wherein one or more commonly encountered antigens are delivered using particle delivery methods, each such antigen being delivered to a discrete target skin site in the individual. The various target skin sites are then assessed to determine the presence or absence of a suitable localized skin immune reaction, e.g., localized induration and/or erythema. The presence of a localized skin immune reaction (e.g., induration and/or erythema) at the test site(s) is indicative of a typical DTH reaction to the various antigens. The absence of a localized skin immune reaction at the test site(s) is indicative of anergy.

It is an advantage of the present methods that such immunodiagnostic tests can be conducted quickly and effectively with a significantly reduced amount of pain and discomfort to the individual. In addition, particle delivery methods allow for the targeted delivery of the various antigens and allergens to the interstitial spaces of the epidermis or dermis, or allow for intracellular delivery into targeted cells. It is also an advantage of the invention that simple visual assessment of localized skin immune reactions can be used in lieu of current diagnostic methods which can entail costly and detailed immunological assays of serum antibody levels, in vitro analyses of peripheral blood lymphocyte proliferation responses, cytokine release assays, or measurement of serum antigen levels. The methods of the present invention can also be readily adapted to assess early exposure and clinical status to viral disease such as HIV, immunization status to various etiological agents, diagnose a neoplastic condition, assess allergies in individuals, or diagnose clinical anergy in immunocompromised individuals.

These and other objects, aspects, embodiments and advantages of the present invention will readily occur to those of ordinary skill in the art in view of the disclosure herein.

DETAILED DESCRIPTION OF THE PREFERRED EMBODIMENTS

Before describing the present invention in detail, it is to be understood that this invention is not limited to particularly exemplified diagnostic particle formulations, antigens, allergens or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a particle" includes a mixture of two or more such particles, reference to "an antigen" or "an allergen" includes mixtures of two or more such agents, and the like.

A. Definitions

Unless defined otherwise, all technical and scientific terms used herein have the same meaning as commonly understood by one of ordinary skill in the art to which the invention pertains. The following terms are intended to be defined as indicated below.

An "immunological response" or "immune response" against a selected agent or a composition of interest is the development in an individual of a humoral and/or a cellular immune response to molecules (e.g., antigens or allergens) present in the agent or composition of interest. For purposes of the present invention, a "humoral immune response" refers to an immune response mediated by antibody molecules, while a "cellular immune response" is one mediated by T-lymphocytes and/or other white blood cells.

An individual previously exposed (sensitized) to a particular immunologic agent (e.g., an antigen or allergen) will typically exhibit a detectable immunological response upon subsequent encounters with that agent. When the subsequent encounter takes place in skin tissue, the detectable immunological response can entail a "localized skin immune reaction" at the point of encounter which is due to local injury to normal self tissue brought about by components of the immunological response directed against the agent. There are generally four major types of localized skin immune reactions that can be classified based on the principal pathogenic mechanism responsible for the localized skin cell/tissue injury. The first type of localized skin immune reaction is termed "Type I immediate hypersensitivity" which is caused by IgE antibodies, mast cells and their mediators (vasoactive amines, lipid mediators and cytokines). Type I hypersensitivity reactions are generally directed against allergens such as plants, chemicals, materials, and foods. A second type of hypersensitivity, also caused by antibodies, is termed "Type II antibody-mediated hypersensitivity." In this case, antibodies other than IgE (i.e., IgM and IgG) can cause tissue injury by recruiting and activating leukocytes (neutrophils, macrophages) and by activating the complement system. The third type of skin reaction, "Type III immune complex-mediated hypersensitivity" involves tissue damage brought about by immune complexes of circulating antigens and IgM or IgG antibodies which activate complement and recruit and activate leukocytes. Type II and III hypersensitivity reactions are generally directed against antigens associated with infectious pathogens, cancers, autoimmune disorders, or incompatible cells such as blood cells (e.g., blood transfusion or Rh incompatibility) or tissue cells (e.g., transplanted organs or tissue). The fourth type of skin reaction, termed "Type IV T cell-mediated hypersensitivity" involves local skin tissue damage brought about by CD4$^+$ T cells, activated macrophages and cytokines (delayed type hypersensitivity or DTH) or CD8$^+$ T cells and cytokines (T cell-mediated cytolysis). Type IV hypersensitivity reactions are also generally directed against antigens associated with infectious pathogens, cancers or autoimmune disorders, as well as agents involved in contact dermatitis conditions. For the purposes of the invention, reference to "a localized skin immune reaction" encompasses any one of the four major types of hypersensitivity reactions unless expressly stated otherwise.

In the practice of the invention, the presence or absence of localized skin immune reactions can be readily assessed according to known clinical procedures. For example, such skin reactions can be assessed qualitatively, e.g., visually. A Type I skin reaction is usually in the form of urticaria and a wheal which appears within minutes (the early phase reaction) after antigen challenge, developing into inflammation within about 6–24 hours (the late phase reaction). The pathogenic damage associated with this cutaneous reaction is generally characterized by edema, vascular dilation, and local smooth muscle contraction. A Type II skin reaction is typically in the form of local induration and erythema occurring over a period of 4–48 hours after antigen challenge. A Type III skin reaction is usually in the form of an Arthus reaction (local cutaneous vasculitis) which occurs within about 2–6 hours of the antigen challenge. Pathogenic damage includes necrotizing vasculitis. Type IV skin reactions usually occur within about 24–48 hours of antigen challenge, and are typified by induration and/or erythema. Pathogenic tissue damage includes perivascular cellular infiltrates and edema. All four of these major types of skin reactions can, of course, also be assessed quantitatively using calipers, ultrasound, chromameter and laser-Doppler techniques well known to those skilled in the art. Accordingly, the present invention is not limited by the manner in which the localized skin immune response is assessed or otherwise characterized.

An "antigen" refers to any immunogeneic moiety or agent, generally a macromolecule, which can elicit an immunological response in an individual. The term may be used to refer to an individual macromolecule or to a homogeneous or heterogeneous population of antigenic macromolecules. As used herein, "antigen" is generally used to refer to a hapten, an organic or inorganic substance, or a protein molecule or portion thereof which contains one or more epitopes. For purposes of the present invention, antigens can be obtained or derived from any known virus, bacteria, parasite or fungal pathogen, a plant, or from man-made or naturally occurring inorganic or organic material. The term also intends any of the various tumor-specific antigens and antigens associated with autoimmune diseases. Furthermore, for purposes of the present invention, an "antigen" includes a protein having modifications, such as deletions, additions and substitutions (generally conservative in nature) to the native sequence, so long as the protein maintains sufficient immunogenicity. These modifications may be deliberate, for example through site-directed mutagenesis, or may be accidental, such as through mutations of hosts which produce the antigens.

In various aspects of the invention, the antigen contains one or more T cell epitopes. A "T cell epitope" refers generally to those features of a peptide structure which are capable of inducing a T cell response. In this regard, it is accepted in the art that T cell epitopes comprise linear peptide determinants that assume extended conformations within the peptide-binding cleft of MHC molecules, (Unanue et al. (1987) *Science* 236:551–557). As used herein, a T cell epitope is generally a peptide having at least about 3–5 amino acid residues, and preferably at least 5–10 or more amino acid residues. The ability of a particular antigen to stimulate a cell-mediated immunological response may be determined by a number of well-known assays, such as by lymphoproliferation (lymphocyte activation) assays, CTL cytotoxic cell assays, or by assaying for T-lymphocytes specific for the antigen in a sensitized subject. See, e.g., Erickson et al. (1993) *J. Immunol.* 151:4189–4199; and Doe et al. (1994) *Eur. J. Immunol.* 24:2369–2376.

In other aspects of the invention, the antigen contains one or more B cell epitopes. A "B cell epitope" generally refers to the site on an antigen to which a specific antibody molecule binds. The identification of epitopes which are able to elicit an antibody response is readily accomplished using techniques well known in the art. See, e.g., Geysen et al. (1984) *Proc. Natl. Acad. Sci. USA* 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) *Molecular Immunology* 23:709–715 (technique for identifying peptides with high affinity for a given antibody).

An "allergen" is an antigen which can initiate a state of hypersensitivity, or which can provoke an immediate hypersensitivity reaction in an individual already sensitized with the allergen. Allergens are commonly proteins or chemicals bound to proteins which have the property of being allergenic; however, allergens can also include organic or inorganic materials derived from a variety of man-made or natural sources such as plant materials, metals, ingredients in cosmetics or detergents, latexes, or the like. Allergens can elicit any type of hypersensitivity reaction in a sensitized individual. For example, penicillin allergies can manifest as all four types (Type I–IV) f hypersensitivity reactions, contact dermatitis can manifest as a Type IV reaction, and gluten allergy can manifest as a Type III reaction. However, allergens typically are associated with Type I immediate hypersensitivity reactions in sensitized individuals.

As used herein, the term "anergy" refers to either a diminished immune reaction, or the absence of an immune reaction to an antigen as revealed by the lack of an appropriate immune response (as detectable by a reduced localized skin immune reaction to a diagnostic antigen or allergen as administered according to the present invention). Anergy can further entail a reversible antiproliferative state which results in decreased responsiveness of an immune cell or cells to an antigen.

Particles which comprise an antigen or allergen are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate compositions. Examples of suitable carriers include water, silicone, gelatin, waxes, and like materials. Examples of normally employed "excipients" include pharmaceutical grades of dextrose, sucrose, lactose, trehalose, mannitol, sorbitol, inositol, dextran, starch, cellulose, sodium or calcium phosphates, calcium carbonate, calcium sulfate, sodium citrate, citric acid, tartaric acid, glycine, high molecular weight polyethylene glycols (PEG), and combinations thereof.

The terms "individual" and "subject" are used interchangeably herein to refer to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly.

B. General Methods

In the practice of the methods of the invention, particulate compositions are provided with comprise an antigen or allergen of interest. If an antigen is used, it will preferably be of associated with a pathogen, such as a viral, bacterial or parasitic pathogen, or the antigen will be a tumor- or cell surface-specific antigen.

Tumor-specific antigens include, but are not limited to, any of the various MAGEs (melanoma associated antigen E), including MAGE 1, MAGE 2, MAGE 3 (HLA-A1 peptide), MAGE 4, etc.; any of the various tyrosinases (HLA-A2 peptide); mutant ras; mutant p53; and p97 melanoma antigen. Other tumor-specific antigens include the Ras peptide and p53 peptide associated with advanced cancers, the HPV 16/18 and E6/E7 antigens associated with cervical cancers, MUC1-KLH antigen associated with breast carcinoma, CEA (carcinoembryonic antigen) associated with colorectal cancer, gp100 or MART1 antigens associated with melanoma, and the PSA antigen associated with prostate cancer. The p53 gene sequence is known (see e.g., Harris et al. (1986) *Mol. Cell. Biol.* 6:4650–4656) and is deposited with GenBank under Accession No. M14694. Thus, the present invention can be used to carry out immunodiagnostic methods for diagnosing or assessing cervical, breast, colorectal, prostate, lung cancers, and melanomas.

Other antigens of interest include surface antigens such as the Rhesus or Rh blood group antigens associated with hemolytic disease, and the ABO blood-group antigens.

Suitable viral antigens include, but are not limited to, polynucleotide sequences encoding antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV). By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 and E2. See, e.g., Houghton et al. (1991) *Hepatology* 14:381–388. The sequences encoding each of these proteins, as well as antigenic fragments thereof, will find use in the present methods. Similarly, the coding sequence for the δ-antigen from HDV is known (see, e.g., U.S. Pat. No. 5,378,814).

In like manner, a wide variety of proteins from the herpesvirus family can be used as antigens in the present invention, including proteins derived from herpes simplex virus (HSV) types 1 and 2, such as HSV-1 and HSV-2 glycoproteins gB, gD and gH; antigens from varicella zoster virus (VZV), Epstein-Barr virus (EBV) and cytomegalovirus (CMV) including CMV gB and gH; and antigens from other human herpesviruses such as HHV6 and HHV7. (See, e.g. Chee et al. (1990) *Cytomegaloviruses* (J. K. McDougal, ed., Springer-Verlag, pp. 125–169; McGeoch et al. (1988) *J. Gen. Virol.* 69:1531–1574; U.S. Pat. No. 5,171,568; Baer et al. (1984) *Nature* 310:207–211; and Davison et al. (1986) *J. Gen. Virol.* 67:1759–1816.)

HIV antigens, such as the gp120 sequences for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992); and Modrow et al. (1987) *J. Virol.* 61:570–578) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol, env, tat, vif, rev, nef, vpr, vpu and LTR regions of HIV.

Antigens derived or obtained from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LA1}$, $HIV_{MN}$); $HIV-1_{CM235}$, $HIV-1_{US4}$; HIV-2, among others. See, e.g. Virology, 3rd Edition (W. K. Joklik ed. 1988); Fundamental Virology, 2nd Edition (B. N. Fields and D. M. Knipe, eds. 1991), for a description of these and other viruses.

Suitable bacterial and parasitic antigens are obtained or derived from known causative agents responsible for diseases including, but not limited to, Diptheria, Pertussis, Tetanus, Tuberculosis, Bacterial or Fungal Pneumonia, Cholera, Typhoid, Meningitis, Mononucleosis, Plague, Shigellosis or Salmonellosis, Legionaire's Disease, Lyme Disease, Leprosy, Malaria, Hookworm, Onchocerciasis, Schistosomiasis, Trypamasomialsis, Lesmaniasis, Giardia, Amoebiasis, Filariasis, Borelia, and Trichinosis. Still further antigens can be obtained or derived from unconventional viruses such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

All of the above-reference antigens can be obtained and/or prepared using known methods. For example, substantially pure antigen preparations can be obtained using standard molecular biological tools. That is, polynucleotide sequences coding for the above-described antigens, or molecules containing such antigens, can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. Polynucleotide sequences can also be produced synthetically, rather than cloned.

Yet another convenient method for isolating specific nucleic acid molecules is by the polymerase chain reaction (PCR). Mullis et al. (1987) Methods Enzymol. 155:335–350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used.

Once obtained, the polynucleotide sequences can be expressed in mammalian, bacterial, yeast, or insect expression systems to provide suitable antigen preparations. Peptide antigens can be also produced using a variety of methods known to those skilled in the art. In particular, the antigens can be isolated directly from native sources, using standard purification techniques, or synthesized based on described amino acid sequences or amino acid sequences derived from the DNA sequence of a nucleic acid molecule of interest, via chemical polymer syntheses such as solid phase peptide synthesis. Such methods are known to those skilled in the art. See, e.g., J. M. Stewart and J. D. Young, Solid Phase Peptide Synthesis, 2nd Ed., Pierce Chemical Co., Rockford, Ill. (1984) and G. Barany and R. B. Merrifield, The Peptides: Analysis, Synthesis, Biology, editors E. Gross and J. Meienhofer, Vol. 2, Academic Press, New York, (1980), pp. 3–254, for solid phase peptide synthesis techniques; and M. Bodansky, Principles of Peptide Synthesis, Springer-Verlag, Berlin (1984) and E. Gross and J. Meienhofer, Eds., The Peptides: Analysis, Synthesis, Biology, supra, Vol. 1, for classical solution synthesis.

Suitable allergens for use in the methods of the invention can also be obtained and/or produced using known methods. Classes of suitable allergens include, but are not limited to, pollens, animal dander, grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from rye, ragweed, English plantain, sorrel-dock and pigweed; plant contact allergens include those from poison oak, poison ivy and nettles; common grass allergens include Timothy, Johnson, Bermuda, fescue and bluegrass allergens; common allergens can also be obtained from molds or fungi such as Alternaria, Fusarium, Hormodendrum, Aspergillus, Micropolyspora, Mucor and thermophilic actinomycetes; penicillin and tetracycline are common antibiotic allergens; epidermal allergens can be obtained from house or organic dusts (typically fungal in origin), from insects such as house mites (dermatphagoides pterosinyssis), or from animal sources such as feathers, and cat and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin and sulfonamide allergens; and common insect allergens include bee, wasp and ant venom, and cockroach calyx allergens. Particularly well characterized allergens include, but are not limited to, the major and cryptic epitopes of the Der p I allergen (Hoyne et al. (1994) Immunology 83190–195), bee venom phospholipase A2 (PLA) (Akdis et al. (1996) J. Clin. Invest. 98:1676–1683), birch pollen allergen Bet v 1 (Bauer et al. (1997) Clin. Exp. Immunol. 107:536–541), and the multi-epitopic recombinant grass allergen rKBG8.3 (Cao et al. (1997) Immunology 90:46–51). These and other suitable allergens are commercially available and/or can be readily prepared as extracts following known techniques.

Once obtained, particles comprising the antigen or allergen of interest can be formulated as a particulate composition following general pharmaceutical methods such as by simple evaporation (crystallization), vacuum drying, spray drying or lyophilization. If desired, the particles can be further densified using the techniques described in commonly owned International Publication No. WO 97/48485, incorporated herein by reference. If the allergen is a metal (e.g., nickel), suitably dense metal particles (per se) can be readily formulated. The particulate compositions (comprising the antigen or allergen of interest) can then be delivered from a needleless syringe system such as those described in commonly owned International Publication Nos. WO 94/24263, WO 96/04947, WO 96/12513, and WO 96/20022, all of which are incorporated herein by reference.

Formulation of the particles comprising the antigen or allergen of interest can be carried out using standard pharmaceutical formulation chemistries and methodologies all of which are readily available to the reasonably skilled artisan. For example, compositions containing one or more antigen or allergen of interest can be combined with one or more pharmaceutically acceptable excipient or vehicle. Auxiliary substances, such as wetting or emulsifying agents, pH buffering substances, and the like, may be present in the excipient or vehicle. These excipients, vehicles and auxiliary substances are generally pharmaceutical agents that do not themselves induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

The formulated compositions will include an amount of the antigen or allergen of interest which is sufficient to mount an immunological response, as defined above. An appropriate effective amount can be readily determined by one of skill in the art. Such an amount will fall in a relatively broad range that can be determined through routine trials. The compositions may contain from about 0.1% to about 99.9% of the antigen or allergen. The compositions are either prepared in a particulate form or rendered into particulate form such as by using evaporative drying, vacuum drying, spray drying, freeze drying, spray-freeze drying, supercritical fluid particle formation, or like techniques generally known to those skilled in the art.

Single unit dosages or multidose containers, in which the particles may be packaged prior to use, can comprise a hermetically sealed container enclosing a suitable amount of the particles comprising the antigen or allergen of interest. The particle compositions can be packaged as a sterile formulation, and the hermetically sealed container can thus be designed to preserve sterility of the formulation until use in the methods of the invention. If desired, the containers can be adapted for direct use in the above-referenced needleless syringe systems.

The container in which the particles are packaged can further be labeled to identify the composition and provide relevant dosage information. In addition, the container can be labeled with a notice in the form prescribed by a governmental agency, for example the Food and Drug Administration, wherein the notice indicates approval by the agency under Federal law of the manufacture, use or sale of the antigen or allergen contained therein for human administration.

Delivery of particles comprising antigens or allergens from the above-referenced needleless syringe systems is practiced with particles having an approximate size generally ranging from 0.1 to 250 μm, preferably ranging from about 10–70 μm. Particles larger than about 250 μm can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin tissue. In this regard, optimal particle densities for use in needleless injection generally range between about 0.1 and 25 $g/cm^3$, preferably between about 0.9 and 1.5 $g/cm^3$, and injection velocities generally range between about 100 and 3,000 m/sec. With appropriate gas pressure, particles having an average diameter of 10–70 μm can be accelerated through the nozzle at velocities approaching the supersonic speeds of a driving gas flow.

If desired, these needleless syringe systems can be provided in a preloaded condition containing a suitable dosage of the particles comprising the antigen or allergen of interest. The loaded syringe can be packaged in a hermetically sealed container, which may further be labeled as described above.

Alternatively, if intracellular delivery is desired, the antigens or allergens can be coated onto suitable carrier particles, e.g., gold or tungsten. For example, peptides can be attached to the carrier particle by simply mixing the two components in an empirically determined ratio, by ammonium sulfate precipitation or other solvent precipitation methods familiar to those skilled in the art, or by chemical coupling of the peptide to the carrier particle. The coupling of L-cysteine residues to gold has been previously described (Brown et al. (1980) *Chemical Society Reviews* 9:271–311). Other methods include, for example, dissolving the peptide antigen in absolute ethanol, water, or an alcohol/water mixture, adding the solution to a quantity of carrier particles, and then drying the mixture under a stream of air or nitrogen gas while vortexing. Alternatively, the peptide antigens can be dried onto carrier particles by centrifugation under vacuum. Once dried, the coated particles can be resuspended in a suitable solvent (e.g., ethyl acetate or acetone), and triturated (e.g., by sonication) to provide a substantially uniform suspension.

Following their formation, carrier particles coated with either antigen or allergen preparations are delivered to the target skin site using particle-mediated delivery techniques.

Various particle acceleration devices suitable for particle-mediated delivery are known in the art, and are all suited for use in the practice of the invention. Current device designs employ an explosive, electric or gaseous discharge to propel the coated carrier particles toward target cells. The coated carrier particles can themselves be releasably attached to a movable carrier sheet, or removably attached to a surface along which a gas stream passes, lifting the particles from the surface and accelerating them toward the target. An example of a gaseous discharge device is described in U.S. Pat. No. 5,204,253. An explosive-type device is described in U.S. Pat. No. 4,945,050. One example of a helium discharge-type particle acceleration apparatus is the PowderJect XR® instrument (PowderJect Vaccines, Inc., Madison), Wis., which instrument is described in U.S. Pat. No. 5,120,657. An electric discharge apparatus suitable for use herein is described in U.S. Pat. No. 5,149,655. The disclosure of all of these patents is incorporated herein by reference.

Single dosages of the coated carrier particles can be provided in a suitable container, for example, provided in a length of tubing which contains a dose of the particles coated on an inner surface thereof. Methods for preparing such containers are described in commonly owned U.S. Pat. Nos. 5,733,600 and 5,780,100, the disclosures of which are incorporated herein by reference.

The particle compositions or coated particles are administered to the individual in a manner compatible with the dosage formulation, and in an amount that will be effective for the purposes of the invention. The amount of the composition to be delivered (e.g., about 0.1 μg to 1 mg, more preferably 1 to 50 μg of the antigen or allergen, depends upon the individual to be tested and the particular antigen(s) or allergen(s) being administered. The exact amount necessary will vary depending on the age and general condition of the individual to be treated, and an appropriate effective amount can be readily determined by one of skill in the art upon reading the instant specification.

The instant methods for assessing humoral and cellular immune responses in an individual find broad application in the field of immunodiagnostics, such as in routine tuberculosis (TB) testing, Rh blood-factor incompatibility, clinical assessments of immunization, and viral or bacterial pathogen exposure (e.g., HBV exposure and HBV immunization status, HIV exposure when CMI precedes seroconversion, and HSV or HPV exposure); and in clinical detection of neoplasia that express known tumor-specific antigens. Although broadly applicable to these and any other immunodiagnostics, the method of the invention is exemplified with respect to assessing a CMI response against a viral recall antigen.

In order to assess the immunization status of an individual previously immunized against a viral agent, the following method is carried out. A pharmaceutical grade recall antigen from the viral agent is obtained, combined with a suitable excipient, and the resulting mixture is dried using a simple evaporative, vacuum-drying, freeze-drying or spray-drying method to obtain particles comprising the viral antigen. If necessary, densification techniques are used to obtain particles having sufficient density characteristics, and classification techniques can be used to obtain a population of particles having a desired average size.

The particles are loaded into a needleless syringe device (e.g., the device described in International Publication No. WO 94/24263), and a suitable dose of the particles are accelerated from the device into a target skin site in the individual, typically into arm. The test site is selected to provide sufficient surface area for the test, and is preferably cleansed with an alcohol swab prior to delivery. Approximately 24 to 48 hours after delivery, the test site is observed for signs of a localized skin immune reaction (e.g., induration and/or erythema). The size of the indurated area is visually assessed and palpated with gentle finger stoking, and measurements are taken across two diameters at right angles to each other. The average diameter is then recorded and compared against established criteria. The presence of an area of induration/erythema having sufficient magnitude is indicative of a CMI response against the recall antigen, and establishes a positive immunization status against the viral agent.

A substantially similar technique can be used to diagnose or monitor infection with, or demonstrate exposure to an infectious disease such as in HIV, hepatitis B or hepatitis C infection. That is, the methods of the present invention provide a tool with which to asses $CD8^+$(cytotoxic) T cell activity in a skin test analogous to a conventional delayed-type hypersensitivity (DTH) reaction. This skin test allows for an evaluation of the activation status of $CD8^+$cells during acute viral infection and of memory $CD8^+$cells in a chronically active immunopathological disease or infection. The test also provides for a rapid diagnostic tool to confirm exposure to an infectious disease such as HIV within a short window of time, for example as quickly as ten days from initial exposure. The basis for the test is a peptide-induced, $CD8^+$-specific DTH reaction brought about by administering particulate peptides to the skin using either the particle-mediated delivery or needleless injection techniques as described herein above. In this regard, a peptide-induced skin test has been described, wherein conventional needle & syringe delivery techniques were used to administer aqueous virus peptide compositions to the sub-cutaneous area of mouse foot pads. Kündig et al. (1992) *Proc. Natl. Acad. Sci.* USA 89:7757–7761. The present technique represents a substantial advance over the Kündig method in that the peptides are provided in a stable, dried powder form and are administered directly into the skin, either to the extracellular spaces when administered using a needleless syringe technique, or directly into cells when administered using a particle-mediated delivery technique.

In this test procedure, one or more virus-specific peptides (each containing a suitable T cell epitope) are obtained and, optionally, combined with a suitable excipient. Because of MHC (HLA)-restricted antigen presentation, either specific immunodominant MHC class I-binding peptides are used that contain a major CTL epitope (if the HLA type of the individual is known), or a cocktail of the different peptides encompassing the major known CTL epitopes are used (to provide a more generally applicable test). If the peptides are to be delivered via needleless syringe, they can be dried using a simple evaporative, vacuum-drying freeze-drying or spray-drying method to obtain suitable particles. As above, densification techniques can be used to obtain particles having sufficient density characteristics, and classification techniques can be used to obtain a population of particles having a desired average size. The particles are then loaded into a needleless syringe device (e.g., the device described in International Publication No. WO 94/24263), and a suitable dose of the particles are accelerated from the device into a target skin site in the individual, typically into arm.

If intracellular delivery is desired, the peptides can be coated onto suitable carrier particles using known techniques. For example, the peptides can be attached to carrier particles by simply mixing the two components in an empirically determined ratio, by ammonium sulfate precipitation or other solvent precipitation methods familiar to those skilled in the art, or by chemical coupling. Alternatively, the peptides can be dissolved in absolute ethanol, water, or an alcohol/water mixture, added to a quantity of carrier particles, and then dried; or the peptides can be dried onto carrier particles by centrifugation under vacuum. The coated carrier particles are then loaded into an acceleration device suitable for particle-mediated delivery (e.g., the device described in U.S. Pat. No. 5,204,253, or the PowderJect XR® instrument (PowderJect Vaccines, Inc., Madison, Wis.), described in U.S. Pat. No. 5,120,657), and a suitable dose is accelerated a target skin site in the individual, typically into arm.

If the method is used to assess exposure to HIV, suitable peptides would include, but are not limited to those including an HIV-1 env T-cell epitope (e.g., RIQRGPGRAFVTIGK (SEQUENCE ID NO.1), NCGGEFFY CNS (SEQUENCE ID NO.2), or KNCGEFFYCNS (SEQUENCE ID NO.3)), an HIV-1 gag T-cell eptiope (e.g., NPPIPVGEIYK (SEQUENCE ID NO. 4), NPPIPVGEIYKRWII (SEQUENCE ID NO. 5), or PVGEIYKRWII (SEQUENCE ID NO. 6)), an HIV-1 gag p 17 B8-restricted CTL epitope (e.g., GGKKKYKL (SEQUENCE ID NO. 7)), an HIV-1 gag p 17 A2-restricted CTL epitope (e.g., SYLNTVATL (SEQUENCE ID NO. 8)), or an HIV-1 pol CTL epitope (e.g., ILKEPVHGV (SEQUENCE ID NO. 9) or TYPDINQML (SEQUENCE ID NO. 10)). Other suitable T-cell epitope-containing HIV peptides are described in U.S. Pat. No. 5,700,635; European Patent Application No. 0907370; and in International Publication Nos. WO 91/04051, WO 96/20006, WO 97/34621, and WO 9733602, the disclosures of which patent, patent application and publications are incorporated herein by reference in their entirities.

The target skin sites are then assessed for evidence of a Type IV DTH response as manifested by induration and erythema. More particularly, approximately 24 to 48 hours after delivery, the test site is observed for signs of a localized skin immune reaction (e.g., induration and/or erythema). The size of the indurated area can be visually assessed and palpated with gentle finger stoking, and measurements taken across two diameters at right angles to each other. The average diameter is then recorded and compared against established criteria. The presence of an area of induration/erythema having sufficient magnitude is indicative of a peptide-induced, $CD8^+$-specific DTH reaction, which in turn can be used to establish exposure to the infectious disease (e.g., HIV).

The instant methods for assessing an allergic condition in an individual can be carried out using any one or more suspected allergens, the selection of which will generally be dictated by the test parameters. For example, these methods can be used to confirm the presence of immediate-type hypersensitivity to foreign substances (allergens) suspected from an individual's history or to confirm allergies to commonly encountered allergens such as pollens, grasses, molds, antibiotics, and a variety of foods; to determine whether environmental allergens are indicated in chronic or persistent cases of asthma, rhinorrhea, bronchospasm, urticaria, eczema, or anaphylaxis; or to document immediate hypersensitivity prior to conducting other allergy testing, such as provocation testing (bronchial provocation, oral food provocation), or prior to allergy desensitization therapy.

Particle formulations are derived from extracts comprising a suitable allergens as discussed above. A needleless syringe device is then used to deliver the allergen-containing particles to a predetermined skin target site, generally on the back or volar aspect of the forearm. If more than one allergen is being tested, discrete particle formulations can be delivered to discrete target sites, generally at least about 2 cm apart from adjacent sites. Up to about 30 different allergens can be delivered in this manner in any one clinical procedure. If desired, negative and positive controls can be included, such as where particles are delivered which comprise a non hypoallergenic substance (negative control) and histamine (positive control) are used. Alternatively, a cocktail of two or more allergens can be delivered in a single particle formulation and used as a triage tool to quickly discriminate whether or not an individual is atopic (allergic). In this sort of method, the particle formulation would include a mixture of two or more common indoor allergens (e.g., house dust mite, cat dander, mold) and/or outdoor allergens (e.g., weed, tree and grass pollens).

The test sites are then visually examined for a localized skin immune reaction (e.g., a wheal and flare reaction), generally maximal at about 15–20 minutes post delivery of the allergens. The largest diameters or transverse diameters of each wheal are taken, and recorded. Generally, a wheal of at least about 5 mm with accompanying erythema (flare) constitutes a positive test, indicating an allergic condition to the allergen. p The instant method for assessing DTH response in an individual find broad application in clinical monitoring, staging and diagnosis procedures, such as in methods for assessing the immunocompetence of an individual, monitoring the nutritional status of an individual, and detecting a disease, disorder or condition in an individual. One specific application involves evaluation of an individual suspected of having primary or acquired immune deficiency disorders in which cell-mediated immunity is decreased or absent (characterized as a state of anergy). In general, these methods rely upon the correlation between the failure to mount sufficient DTH response against a panel of delayed hypersensitivity test antigens. The methods entail delivering a panel of discrete antigens to discrete skin target sites in the individual, and then assessing the test sites for the presence or absence of a typical DTH reaction (induration and/or erythema) as described above.

The panel of antigens can be comprised of any assortment of antigens, generally those antigens that the individual is considered to have been sensitized to from prior contact. An exemplary panel of antigens includes particles formed from the following antigen solutions: Tetanus Toxoid Antigen (e.g., prepared from culture filtrate of *Clostridium tetani*), inactivated and detoxified with formaldehyde; Diphtheria Toxoid Antigen (e.g., prepared from culture filtrate of *Corynebacterium diphtheriae*), inactivated and detoxified with formaldehyde; Streptococcus Antigen (culture filtrate of Streptococcus Group C), inactivated with phenol; Tuberculin, Old (culture filtrates of *Mycobacterium tuberculosis* C, D, and PN and *Mycobacterium bovis*); Candida Antigen (culture filtrate of *Candida albicans*), inactivated with phenol; Trichophytin Antigen (culture filtrate of *Trichophyton mentagrophytes*), inactivated with phenol; and Proteus Antigen (culture filtrate of *Proteus mirabilis*), inactivated with phenol. This panel of antigens is only exemplary, and is not limiting in the instant invention. Numerous other panels of antigens can be readily determined by the reasonably skilled artisan upon reading the instant specification.

Approximately 24–48 hours after delivery, each test site is visually assessed for signs of appropriate localized skin immune responses to the antigens, palpated, and areas of induration/erythema measured. Nonresponsiveness (anergy) to all antigens is indicative of a reduced immunocompetence in the individual, and can be used as a screen to warrant further testing in the individual.

C. Experimental

Below are examples of specific embodiments for carrying out the methods of the present invention. The examples are offered for illustrative purposes only, and are not intended to limit the scope of the present invention in any way.

Efforts have been made to ensure accuracy with respect to numbers used (e.g., amounts, temperatures, etc.) but some experimental error and deviation should, of course, be allowed for.

EXAMPLE 1

In order to evaluate a Type IV localized skin immune reaction following delivery of particles comprising tuberculin/purified protein derivative (PPD) to guinea pigs previously vaccinated with Bacillus Calmette-Guérin (BCG), the following study is carried out. Specifically, local skin reaction as manifested in erythema or duration following delivery of PPD is assessed. Built-in control consists of a comparison against local skin reaction following intradermal administration of PPD with a conventional needle/syringe.

Species

Guinea pigs (Duncan Hartley or similar); Standard test weight (n=16 total).

Test Compound(s)

Tuberculin/PPD (available form Medeva). For delivery from a needleless syringe, PPD is formulated into powder using appropriate excipients, and the resulting particles sized accordingly. (Excipient: 100% mannitol or 90% mannitol/10% trehalose, freeze dried into powder and reprocessed using compression and grinding; total payload; 1 mg; particle size: <53 microns; tuberculin doses: as shown in Table).

For needle/syringe (intradermal) delivery, the PPD is used as directed, as in the standard screening procedure.

Test Device

A Dermal PowderJect® needleless powder injection system (model: standard Phase I, obtained from PowderJect Pharmaceuticals plc., Oxford, UK), operated at a pressure of 40 bar.

Sighting Study

Appropriate conditions for the PowderJect® needleless powder injection system are obtained by conducting a sighting study on two 2 naïve guinea pigs prior to the main experiment. The reformulated tuberculin/PPD is delivered onto clipped sites using several device conditions. Sites are evaluated over the following several days, and any device-related erythema is noted.

Main Study, Study Groups

For the main part of the study, the animals are divided randomly into the following four (4) study groups, depending on whether the animals have been pre-vaccinated with BCG (n=4 for each group):

| Group | Pre-Treatment | Tuberculin Dose (U) For PowderJect sites |
|---|---|---|
| I | BCG-positive | 5 |
| II | BCG-positive | 25 |
| III | BCG-negative | 5 |
| IV | BCG-negative | 25 |

Experimental Design and Procedures

Prior to the start of the study, animals in study groups I and II are vaccinated with BCG. The animals in study group III and IV are naïve to BCG (GCG-negative).

On the day prior to the start of the study, two 50 mm diameter areas are clipped on each of the right and left flanks of each guinea pigs.

The study involves needleless delivery of two replicate doses of reformulated tuberculin/PPD, as shown in the Table above. As a control, each animal further receives two intradermal injections (via needle-syringe) of 5 U tuberculin/PPD. The sites of administration are separated such that no site-to-site cross reactivity occurs. The same batch of tuberculin/PPD is used for the needleless and conventional needle-syringe administrations.

The sites of administration are evaluated for any signs of local cutaneous response at 6, 24, 48 and 72 hours (or until any local response is resolved). Any responses are noted, and the sizes of the reactions measured. In particular, local erythema, induration (palpalable or observable), or other signs of a DTH response are graded, measured and photographed. The animals are observed on a daily basis for any signs of distress or infection.

EXAMPLE 2

In order to evaluate a Type I localized skin immune reaction following dermal needleless delivery of particles comprising reformulated allergens to naïve and sensitized individuals, the following study is carried out. Specifically, local skin reactions are assessed for evidence of IgE-dependent immediate hypersensitivity responses to several reformulated allergens and controls. IgE-dependent immediate hypersensitivity is generally manifested by a wheal and flare response occurring approximately 15 minutes after allergen delivery.

Subjects 18 human subjects are chosen according to the following inclusion criteria: 6 subjects have a known to latex; 6 subjects have a known allergy to stinging nettle; and 6 subjects have no known allergy to latex or stinging nettle. Pregnancy or lactation represent exclusion criteria.

Test Compound(s)

Allergens (obtained from ALK, Denmark): Latex extract; and Stinging nettle extract. Controls (obtained from ALK, Denmark): Positive control (histamine); and Negative control (buffered saline). These come in a glycerol base.

Test compounds are reformulated into powder through dilution, addition of Tween, a suitable cryoprotectant (PEG) and an excipient (mannitol). The mixtures are separately lyophilised, then compressed, ground, and sieved (<53 micron) to form appropriate particle compositions. 1 mg payloads are weighed into drug cassettes prior to delivery from a needleless syringe device.

Test Device

A Dermal PowderJect® needleless powder injection system (model: standard Phase I, obtained from PowderJect Pharmaceuticals plc., Oxford, UK), operated at a pressure of 40 bar.

Experimental Design and Procedures

Each individual receives needleless injections with both allergens and both controls at four separate sites on the volar aspect of the left forearm. Skin prick tests for both antigens and both controls are administered to the right forearm.

The sites are evaluated over the following 60 minutes for evidence of wheal and flare reaction. Any reactions on either arm are noted and photographed at least 15 minutes after administration of the compounds. The extent and duration of erythema and/or induration is also noted for each site.

EXAMPLE 3

In order to evaluate a Type II localized skin immune reaction following delivery of particles comprising red blood cells isolated Rh-antigen, the following study is carried out. Specifically, local skin reaction as manifested in erythema or induration following delivery of the Rh antigen is assessed.

Subjects

Healthy human subjects are selected according to routine inclusion criteria. Known Rh-positive and Rh-negatives can be included as controls.

Test Compound(s)

Isolated red blood cell Rh-antigen is obtained from a commercial source. The test compounds are reformulated into powder using appropriate excipients, and the resulting particles are sized accordingly. (Excipient: 100% mannitol, or 90% mannitol/10% trehalose, freeze-dried into powder and reprocessed using compression and grinding).

Test Device

A Dermal PowderJect® needleless powder injection system (model: standard Phase I, obtained from PowderJect Pharmaceuticals plc., Oxford, UK), operated at a pressure of 40 bar.

Experimental Design and Procedures

Each individual receives needleless injections with the Rh-antigen on the volar aspect of the forearm. Several days after administration, the test site is assessed for signs of a Type II skin reaction. Any such cutaneous responses are noted, and the sizes of the reactions measured. In particular, local erythema, induration (palpable or observable), or other signs of an immune response are graded, measured and photographed. Skin reactions are expected in Rh-negative individuals previously exposed to Rh-antigen through pregnancy or blood transfusion. No reactions are expected in either known Rh-positive individuals or Rh-negative individuals not previously exposed. As an internal check, a reaction can be elicited in this latter group using the above-described procedures to administer a Rh-antigen prime followed 4–6 weeks later by a Rh-antigen challenge.

EXAMPLE 4

In order to evaluate a Type III localized skin immune reaction following delivery of particles comprising glutin, the following study is carried out. Specifically, local skin reaction as manifested in local cutaneous vasculitis following delivery of the glutin antigen is assessed.

Subjects

Healthy human subjects are selected according to routine inclusion criteria. Generally, a first experimental group is comprised of individuals having dermatitis herpetiformis, and a second experimental group is comprised of normal individuals.

Test Compound(s)

Glutin antigen is obtained from a commercial source. Test compounds are reformulated into powder through dilution, addition of Tween, a suitable cryoprotectant (PEG) and an excipient (mannitol). The mixtures are separately lyophilized, then compressed, ground, and sieved to form appropriate particle compositions.

Test device

A Dermal PowderJect® needleless powder injection system (model: standard Phase I, obtained from PowderJect Pharmaceuticals plc., Oxford, UK), operated at a pressure of 40 bar.

Experimental Design and Procedures

Each individual receives needleless injections with the glutin antigen on the volar aspect of the forearm. Several days after administration, the test site is assessed for signs of a Type III skin reaction. Any such cutaneous responses are noted, and the size and extent of the reactions measured.

EXAMPLE 5

In order to assess whether a particle delivery system can be used to administer a mixture of common allergens into skin for a rapid diagnostic triage tool for assessing general allergy status, the following study was carried out.

Subjects 18 healthy human subjects aged 18–50 years old were selected according to the following inclusion criteria: 12 subjects were atopic (reported a history of one or more allergic conditions) and 6 subjects non-allergic ("control"), having no reported history of allergic conditions.

Test Compound(s)

Three different individual skin prick test allergens were obtained from ALK (UK) consisting of extracts from: (1) a six-grass mixture, (2) house dust mite (dermatphagoides pterosinyssis); and (3) cat dander. These allergens were administered individually by a standard skin prick administrator, or combined to provide the triage allergen formulation. More particularly, a powdered triage allergen formulation was made by combining the three extracts with an excipient, lyophilization, compression, grinding, and then sieving to provide a particulate composition. For skin prick tests, the administrator was inserted into the allergen extract prior to delivery to the test site. For particle delivery, approximately 1 mg payloads of the powdered triage allergen formulation was weighted into drug cassettes prior to delivery from a needleless syringe device. A placebo particulate composition was made from the excipient, and 1 mg payloads were loaded into drug cassettes as above.

Test Devices

A Dermal PowderJect® needleless powder injection system (model: standard Phase I, obtained from PowderJect Pharmaceuticals plc., Oxford, UK), operated at a pressure of 40 bar was used to administer the triage or placebo particle compositions. A standard skin prick test administrator was used to administer the individual allergen extracts in the skin prick comparator.

Experimental Design and Procedures

Each individual received a needleless injection of the powdered triage allergen formulation, a needleless injection of the powdered placebo (excipient), and individual skin prick test (SPT) administrations of each allergen extract, all delivered to the volar surface of the right forearm (SPT) or volar surface of the left forearm (needleless injections). Each site of administration was examined 15 minutes after administration to measure the diameters of induration (wheal) and erythema (flare).

Results 11 of the 18 subjects were found positive (atopic) to at least one of the allergen extracts administered via the skin prick test (SPT). These same 11 subjects were also found positive to the powdered triage allergen formulation administered by the Dermal PowderJect® needleless syringe device. In these 11 atopic subjects, the average wheal (induration) diameter for positive SPT sites was 6.4 mm as compared with an average wheal diameter of 16.8 mm for positive triage formulation sites. No placebo powder sites resulted in any induration, although a mild "collateral" erythema (flare) averaging about 10 mm was generally seen at these placebo sites.

5 of the 18 subjects were found negative in both the individual allergen (SPT) and the powdered triage allergen tests. The remaining 2 subjects were found negative in each of the SPT tests, but were shown to be positive in the powdered triage allergen test. One of these 2 subjects had noted a history of asthma and eczema, although there were no clinically observable symptoms of either condition at the time of the study. The other subject had noted no history of allergic conditions. However, this subject's induration at the powdered triage allergen formulation site was less than one-half of the average (16.8 mm) wheal, signifying the possibility of a weak atopy to the specific allergens used in the test.

These results demonstrate that the Dermal PowderJect® needleless syringe device can be used to deliver an allergen mixture to atopic and control individuals in order to provide a rapid and accurate diagnostic test to distinguish among these patient populations based on a localized skin immune reaction. These results further indicate that the powdered triage allergen formulation delivered by needleless syringe injection is a more sensitive diagnostic test method than the current standard diagnostic method (the skin prick test).

Accordingly, novel immunodiagnostic methods are disclosed. Although preferred embodiments of the subject invention have been described in some detail, it is understood that obvious variations can be made without departing from the spirit and the scope of the invention as defined by the appended claims.

We claim:

1. A method for assessing an immune response against a selected agent in an individual, said method comprising:

(a) accelerating particles comprising dried, particulate antigen derived or obtained from said selected agent into a target skin site in said individual; and (b) assessing the target site to determine the presence or absence of a localized skin immune reaction, wherein the presence of said immune reaction is indicative of an immune response against the selected agent.

2. The method of claim 1, wherein the particles are inert carrier particles coated with a composition comprising the antigen.

3. The method of claim 2, wherein the inert carrier particles are gold particles.

4. The method of claim 1, wherein the particles are accelerated toward the target site using a needleless syringe device.

5. The method of claim 4, wherein the particles are accelerated toward the target site at a velocity of about 100 to 3,000 m/sec.

6. The method of claim 4, wherein the particles have a size predominantly in the range of about 0.1 to 250 µm.

7. The method of claim 1, wherein the antigen is an antigen from a selected pathogenic agent.

8. The method of claim 7, wherein the antigen is a viral or bacterial antigen.

9. The method of claim 8, wherein the antigen is a hepatitis virus antigen.

10. The method of claim 8, wherein the antigen is a human immunodeficiency virus (HIV) antigen.

11. The method of claim 8, wherein the antigen is a papilloma virus antigen.

12. The method of claim 8, wherein the antigen is a herpes virus antigen.

13. The method of claim 8, wherein the antigen is a *Mycobacterium tuberculosis* antigen.

14. The method of claim 1, wherein the selected agent is a cancer antigen.

15. The method of claim 1, wherein the antigen is a red blood cell Rh antigen.

16. The method of claim 1, wherein the particles are delivered into the epidermis or dermis of the individual.

17. The method of claim 1, wherein the antigen is an allergen.

18. The method for assessing an allergic condition in an individual, said method comprising:

(a) accelerating particles comprising dried, particulate allergen into a target skin site in said individual; and (b) assessing the target site to determine the presence or absence of a localized skin immune reaction, wherein presence of said skin reaction is indicative of an allergic condition in the individual.

19. A method for assessing an allergic condition in an individual, said method comprising:

(a) accelerating dried, particulate particles comprising a first allergen into a first target skin site in said individual; and (b) assessing the first target site to determine the presence or absence of a localized skin immune reaction, wherein presence of said skin reaction is indicative of an allergic condition against said allergen.

20. The method of claim 19, wherein step (a) is repeated to deliver particles comprising a further allergen to a second target skin site in the individual, and step (b) entails assessing said first and second target sites for the presence of a localized skin immune reaction.

21. The method of claim 19, wherein the particles are inert carrier particles coated with a composition comprising said first allergen.

22. The method of claim 21, wherein the inert carrier particles are gold particles.

23. The method of claim 19, wherein the particles are accelerated toward the target site using a needleless syringe device.

24. The method of claim 23, wherein the particles are accelerated toward the target site at a velocity of about 100 to 3,000 m/sec.

25. The method of claim 23, wherein the particles have a size predominantly in the range of about 0.1 to 250 µm.

26. A method for assessing a delayed type hypersensitivity (DTH) reaction in an individual, said method comprising:

(a) administering a plurality of dried, particulate recall antigens to said individual, wherein each said recall antigen is administered to a discrete target skin site in the individual, and administration is carried out by accelerating discrete populations of particles comprising said recall antigens into said discrete target sites; and (b) assessing said target sites to determine the presence or absence of a localized skin immune reaction as an indication of a DTH reaction to one or more of said recall antigens.

27. The method of claim 26, wherein each said particle population comprises inert carrier particles coated with a composition comprising one of said discrete recall antigens.

28. The method of claim 27, wherein the inert carrier particles are gold particles.

29. The method of claim 26, wherein the particles are accelerated toward said target sites using a needleless syringe device.

30. The method of claim 29, wherein the particles are accelerated toward the target site at a velocity of about 100 to 3,000 m/sec.

31. The method of claim 29, wherein the particles have a size predominantly in the range of about 0.1 to 250 µm.

* * * * *

```
                              SEQUENCE LISTING

<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:synthetic
      construct

<400> SEQUENCE: 1

Arg Ile Gln Arg Gly Pro Gly Arg Ala Phe Val Thr Ile Gly Lys
 1               5                  10                  15

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:synthetic
      construct

<400> SEQUENCE: 2

Asn Cys Gly Gly Glu Phe Phe Tyr Cys Asn Ser
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence:synthetic
      construct

<400> SEQUENCE: 3

Lys Asn Cys Gly Glu Phe Phe Tyr Cys Asn Ser
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence:synthetic
      construct

<400> SEQUENCE: 4

Asn Pro Pro Ile Pro Val Gly Glu Ile Tyr Lys
 1               5                  10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:synthetic
      construct

<400> SEQUENCE: 5

Asn Pro Pro Ile Pro Val Gly Glu Ile Tyr Lys Arg Trp Ile Ile
 1               5                  10                  15
```

```
<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence:synthetic
      construct

<400> SEQUENCE: 6

Pro Val Gly Glu Ile Tyr Lys Arg Trp Ile Ile
 1               5                  10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:synthetic
      construct

<400> SEQUENCE: 7

Gly Gly Lys Lys Lys Tyr Lys Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:synthetic
      construct

<400> SEQUENCE: 8

Ser Leu Tyr Asn Thr Val Ala Thr Leu
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:synthetic
      construct

<400> SEQUENCE: 9

Ile Leu Lys Glu Pro Val His Gly Val
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:synthetic
      construct

<400> SEQUENCE: 10

Thr Pro Tyr Asp Ile Asn Gln Met Leu
 1               5
```